(12) United States Patent
Brand et al.

(10) Patent No.: US 7,078,571 B2
(45) Date of Patent: Jul. 18, 2006

(54) PREPARATION OF 1,3-DI-HALO-SUBSTITUTED BENZENE DERIVATIVES

(75) Inventors: Stefan Brand, Schriesheim (DE); Daniel Decker, Liederbach a. Ts. (DE); Thomas Wessel, Niederdorfelden (DE)

(73) Assignee: Clariant GmbH, Frankfurt (DE)

( * ) Notice: Subject to any disclaimer, the term of this patent is extended or adjusted under 35 U.S.C. 154(b) by 187 days.

(21) Appl. No.: 10/692,927

(22) Filed: Oct. 24, 2003

(65) Prior Publication Data

US 2004/0087816 A1    May 6, 2004

(30) Foreign Application Priority Data

Oct. 25, 2002    (DE)    ............... 102 49 748

(51) Int. Cl.
*C07C 25/13*    (2006.01)
*C07C 43/20*    (2006.01)

(52) U.S. Cl. .............. 568/433; 568/661; 568/663; 568/938; 570/143; 570/201

(58) Field of Classification Search ................ 570/143, 570/201; 568/433, 661, 663, 938
See application file for complete search history.

(56) References Cited

U.S. PATENT DOCUMENTS 4,937,395 A * 6/1990 Litterer et al. ............... 570/142
6,407,029 B1  6/2002 Schiemenz et al. ......... 502/208

FOREIGN PATENT DOCUMENTS

EP    0 598 338    5/1994
EP    1 070 724    1/2001

OTHER PUBLICATIONS

English abstract for EP 0598338, May 25, 1994.
Lock, Chem. Bericht, 1936, 69, pp. 2253-2258.
English translation of G. Lock, "Uber die Abspalting der Aldehydgruppe als Amisensaure aus Aromatischen Aldehyden, III. Mitteil Gemischt-halogen-haltige und Halogen-nitrobenzaldehyde," Barichte Der Deutschen Chamischen Gesellschaft, Bd. 68, pp. 1501-1511 (1935).
English translation of G. Lock, Zur Kenntnis der Cannizzaroschen Reaktion, "Monatahefte Der Chemie" Bd. 55, pp. 307-315 (1930).
English translation of G. Lock, "Uber einige Halogenderivate des Meta-oxy-benzaldehydes," Monatshefte Der Chemie Bd. 67, pp. 320-327 (1936).
English translation of G. Lock, "Uber die Abspaltung der Aldehydgruppe Aus aromatischen aldehyden, I. Mitteil Polychlorbenzaldehyde," Berichte der Deutschen Chemischen Gesellschaft, Bd. 66, pp. 1527-1531 (1933).
English translation of G. Lock, "Uber die Abspaltung der Aldehydgruppe als Ameisensaure aus aromatischen Aldehyden, IV. Mitteil: 2-chlor-6-fluor-und 2, 6-Difluor-benzaldehyd," Berichte der Deutschen Chemischen Gesellschaft, Bd. 69, pp. 2253-2258 (1936).
EP Search Report for EP 03023176, mailed Feb. 4, 2004.
G. Lock, "Uber die Abspalting der Aldehydgruppe als Amisensaure aus Aromatischen Aldehyden, III. Mitteil Gemischt-halogen-haltige und Halogen-nitrobenzaldehyde," Barichte Der Deutschen Chamischen Gesellschaft, Bd. 68, pp. 1501-1511 (1935).
G. Lock, Zur Kenntnis der Cannizzaroschen Reaktion, "Monatahefte Der Chemie" Bd. 55, pp. 307-315 (1930).
G. Lock, "Uber einige Halogenderivate des Meta-oxy-benzaldehydes," Monatshefte Der Chemie Bd. 67, pp. 320-327 (1936).
G. Lock, "Uber die Abspaltung der Aldehydgruppe Aus aromatischen aldehyden, I. Mitteil Polychlorbenzaldehyde," Berichte der Deutschen Chemischen Gesellschaft, Bd. 66, pp. 1527-1531 (1933).
G. Lock, "Uber die Abspaltung der Aldehydgruppe als Ameisensaure aus aromatischen Aldehyden, IV. Mitteil: 2-chlor-6-fluor-und 2, 6-Difluor-benzaldehyd," Berichte der Deutschen Chemischen Gesellschaft, Bd. 69, pp. 2253-2258 (1936).

* cited by examiner

*Primary Examiner*—Fiona T. Powers
(74) *Attorney, Agent, or Firm*—Anthony A. Bisulca

(57) ABSTRACT

A process for preparing 1,3-di-halo-substituted benzene derivatives (II) from 2,6-di-halo-substituted benzaldehydes (I) (where $X_1$, $X_2$ are each independently F, Cl, Br, and $R_1$, $R_2$, $R_3$ are each independently H, halogen, OH, $C_1$–$C_{12}$-alkyl, $CF_3$, CHO, $C_6$–$C_{14}$-aryl, Oalkyl, Oaryl, $NO_2$) by reacting with an alkaline medium, which comprises initially charging the alkaline medium and metering in the 2,6-di-halo-substituted benzaldehyde (I) or initially charging the 2,6-di-halo-substituted benzaldehyde (I) and metering in the alkaline medium

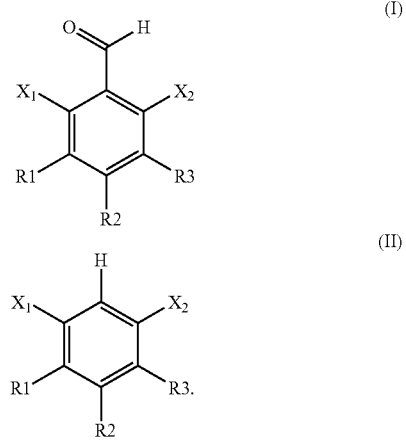

15 Claims, No Drawings

PREPARATION OF 1,3-DI-HALO-SUBSTITUTED BENZENE DERIVATIVES

The present invention relates to an improved process for preparing 1,3-di-halo-substituted benzene derivatives (II) from 2,6-di-halo-substituted benzaldehydes (I) by reacting with an alkaline medium, wherein the alkaline medium is initially charged and the 2,6-di-halo-substituted benzaldehyde (I) is metered in, or the 2,6-di-halo-substituted benzaldehyde (I) is initially charged and the alkaline medium is metered in.

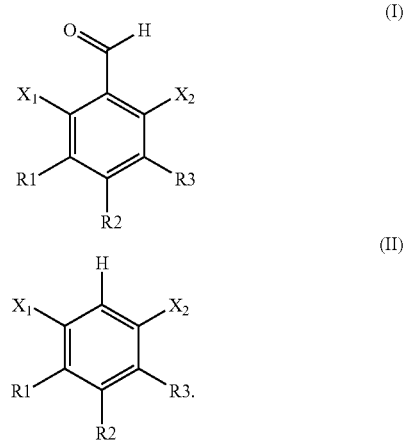

In particular, this invention relates to a process which is an improvement over the prior art, and in which the 1,3-di-halo-substituted benzene derivatives (II) are obtained in high selectivity and yield, and scale-up to production scale satisfies safety requirements.

1,3-Di-halo-substituted benzene derivatives (e.g. 1,3-difluorobenzene) are important intermediates for preparing pharmaceutical and agrochemical products.

Processes for preparing 1,3-di-halo-substituted benzene derivatives (II) are known per se. For example, 1,3-difluorobenzene can be synthesized by catalytic elimination of chlorine starting from 2,4-difluorochlorobenzene (EP-A-598 338). A disadvantage of this procedure is that 2,4-difluorochlorobenzene is obtainable only by process steps which are difficult and complicated from a technical point of view, for example by chlorine/fluorine exchange starting from 2,4-dichloronitrobenzene, followed by denitrating chlorination of the resulting 2,4-difluoronitrobenzene (EP-A-598 338).

As an alternative to preparing 1,3-di-halo-substituted benzene derivatives (II), it is advantageous to use 2,6-di-halo-substituted benzaldehydes (I) as starting materials. For example, in the case of 1,3-difluorobenzene, 2,6-difluorobenzaldehyde is obtainable in high yield starting from 2,6-dichlorobenzaldehyde by chlorine/fluorine exchange (EP-A-1 070 724).

It is already known that 1,3-di-halo-substituted benzene derivatives (II) can be prepared by reacting 2,6-di-halo-substituted benzaldehydes (I) with aqueous alkali (Lock, Chem. Ber. 1936, 69, 2253). However, the procedure described has the disadvantage that all starting materials are initially charged all at once and the reaction mixture is subsequently heated up to the required reaction temperature. The formation of a solid is described and even observed (see comparative examples), which has adverse effects on the selectivity and the yield of the reaction. In the case of the synthesis of 1,3-difluorobenzene from 2,6-difluorobenzaldehyde, only a moderate yield of 61% is described (Lock, Chem. Ber. 1936, 69, 2253). The moderate yield can also be confirmed by comparative experiments (see comparative examples). A further disadvantage is that the simultaneous initial charging of all starting materials before commencement of the reaction is problematic in the scale-up to production scale for safety reasons and thus cannot be realized.

In view of the aforementioned disadvantages of the existing processes, there is need to provide an improved process which does not have any of these disadvantages.

This object is achieved by a process for preparing 1,3-di-halo-substituted benzene derivatives (II) from 2,6-di-halo-substituted benzaldehydes (I) (where $X_1$, $X_2$ are each independently F, Cl, Br, and $R_1$, $R_2$, $R_3$ are each independently H, halogen, in particular F, Cl, Br, OH, $C_1$–$C_{12}$-alkyl, in particular $C_1$–$C_8$-alkyl, $CF_3$, CHO, $C_6$–$C_{14}$-aryl, Oalkyl, Oaryl, $NO_2$) by reacting with an alkaline medium, which comprises initially charging the alkaline medium and metering in the 2,6-di-halo-substituted benzaldehyde (I) or initially charging the 2,6-di-halo-substituted benzaldehyde (I) and metering in the alkaline medium.

Examples of 2,6-di-halo-substituted benzaldehydes (I) which can be used in accordance with the invention include: 2,6-difluorobenzaldehyde, 2-chloro-6-fluorobenzaldehyde, tetrafluoroterephthalaldehyde, 2,4,6-trifluorobenzaldehyde, 4-chloro-2,6-difluorobenzaldehyde, 2,4-dichloro-6-fluorobenzaldehyde, pentafluorobenzaldehyde, 3,5-dichloro-2,4,6-trifluorobenzaldehyde, 2,4,5,6-tetrafluorobenzene-1,3-dicarbaldehyde or 5-chloro-2,4,6-trifluorobenzene-1,3-dicarbaldehyde, to name only a few. Particular preference is given to 2,6-difluorobenzaldehyde, 2-chloro-6-fluorobenzaldehyde and tetrafluoroterephthalaldehyde.

Owing to the sensitivity of benzaldehydes toward atmospheric oxygen, it is advantageous to carry out the reaction under protective gas (e.g. argon or nitrogen).

The alkaline medium used may be aqueous solutions of bases of alkali metals or alkaline earth metals, in particular alkali metal or alkaline earth metal hydroxide or carbonate solutions, for example sodium hydroxide, potassium hydroxide, calcium hydroxide, sodium carbonate, potassium carbonate, or else ammonia, and particular preference is given to aqueous solutions of sodium hydroxide, potassium hydroxide and calcium hydroxide.

The carbonyl group is eliminated in such a way that one mole of formate is formed under the action of the alkaline medium per mole of carbonyl group. The alkaline medium is therefore used in such an amount that at least one mole of the abovementioned bases is used for each mole of carbonyl group of the 2,6-di-halo-substituted benzaldehydes (I) to be eliminated.

The concentration of the alkaline medium used can be selected freely, but should not be too small. In the case of the particularly preferred bases, sodium hydroxide and potassium hydroxide, it is advantageous to select a base concentration in the range from 40 to 50% by weight.

The process can be carried out within the temperature range of from 50 to 215° C., and preference is given to the temperature range of from 70 to 160° C., particular preference to the temperature range from 70 to 110° C.

The 1,3-di-halo-substituted benzene derivatives (II) can be isolated, for example, by steam distillation, by extraction with a water-immiscible solvent (e.g. diethyl ether, methyl tert-butyl ether, toluene, xylene), by crystallization or by chromatographic methods. In the case of reaction products having a boiling point lower than that of water, it is possible to simultaneously distill off the reaction products during the metering-controlled reaction. To achieve very pure 1,3-di-halo-substituted benzene derivatives (II), it is advantageous to subsequently carry out a fractional distillation.

It is to be regarded as very surprising that when the process according to the invention is carried out, the 1,3-di-halo-substituted benzene derivatives (II) are obtained more selectively and in very much higher yield than in the procedure corresponding to the prior art. For instance, yields of >80%, in particular yields of >90%, are achievable by the process according to the invention. Among other advantages, the process according to the invention in particular has the advantage that the conversion of 2,6-di-halo-substituted benzaldehydes (I) to 1,3-di-halo-substituted benzene derivatives (II) can be controlled via the metering rate and the reaction can therefore be interrupted at any time. In addition, the scale-up of the process to the production scale satisfies the safety requirements.

It is also very surprising that this procedure can be applied even to complicated substitution patterns, i.e. dicarbonyl compounds, for example tetrafluoroterephthalaldehyde, which can only be obtained with poor yields by the prior art processes. However, a reaction in accordance with the process according to the invention achieves very good yields (see Example 4), and the crude products likewise also occur in high purity.

The examples and comparative examples which follow serve to illustrate the subject-matter of the invention, without any intention to restrict the invention to these examples.

EXAMPLES

Example 1

Synthesis of 1,3-difluorobenzene from 2,6-difluorobenzaldehyde

A glass flask equipped with stirrer, thermometer, dropping funnel and distillation head with condenser is initially charged at room temperature and under argon with 245 g of water, and 245 g (3.80 mol) of KOH prills (87%) are added with stirring. Once the KOH prills have completely dissolved, the mixture is heated to an internal temperature of 95° C. 500 g (3.52 mol) of 2,6-difluorobenzaldehyde are added dropwise within from 3 to 4 hours. 1,3-Difluorobenzene distills off together with a small amount of water and is collected in an ice-cooled receiver. Subsequently, the mixture is heated to an internal temperature of 120° C. for a further 15 min., in order to distill off last residues of 1,3-difluorobenzene. The distillate is subjected to a phase separation to obtain 380 g (3.33 mol) of 1,3-difluorobenzene (yield 94.6%). The content of 1,3-difluorobenzene is determined by gas chromatography and is greater than 99.0%.

Example 2

Comparative Examples (cf. Lock, Chem. Ber. 1936, 69, 2253). All Starting Materials are Initially Charged all at Once Ratios of amounts as in Lock, Chem. Ber. 1936, 69, 2253.
A glass flask equipped with stirrer, thermometer, dropping funnel and distillation head with condenser is initially charged with ice cooling and under argon with 50 g (0.352 mol) of 2,6-difluorobenzaldehyde and also 345 g (3.07 mol) of aqueous KOH solution (50%), and the formation of a yellow solid is observed. Subsequently, the reaction mixture is heated to from 95 to 100° C., and 1,3-difluorobenzene is distilled off and is collected in a cooled receiver. The distillate is subjected to a phase separation to obtain 21.0 g (0.184 mol) of 1,3-difluorobenzene (yield 52.3%). In the remaining reaction mixture, comparatively large amounts of a yellow solid are observed which could not be characterized further.

Ratios of amounts as in example 1
A glass flask equipped with stirrer, thermometer, dropping funnel and distillation head with condenser is initially charged at room temperature and under argon with 49 g (0.380 mol) of aqueous KOH solution (43.5%) and also 50 g (0.352 mol) of 2,6-difluorobenzaldehyde to form a yellow solid. Subsequently, the reaction mixture is heated to 95° C., and 1,3-difluorobenzene distills off and is collected in a cooled receiver. Subsequently, the mixture is heated to an internal temperature of 120° C. for a further 15 min., in order to distill off last residues of 1,3-difluorobenzene. The distillate is subjected to a phase separation to obtain 24.1 g (0.211 mol) of 1,3-difluorobenzene (yield 59.9%). In the remaining reaction mixture, comparatively large amounts of a yellow solid are observed which could not be characterized further.

Example 3

Synthesis of 1-chloro-3-fluorobenzene from 2-chloro-6-fluorobenzaldehyde

In a glass flask equipped with reflux condenser, stirrer and thermometer, 36 g (0.289 mol) of aqueous KOH solution (45%) are heated to 95° C. under argon. With stirring, 41 g (0.259 mol) of 2-chloro-6-fluorobenzaldehyde are added in small portions (each approx. 2 g) within from 2 to 3 hours. On completion of addition, stirring is continued at 95° C for 15 min. and the mixture is cooled to room temperature. After extraction of a sample of the reaction mixture with methyl tert-butyl ether, complete conversion of 2-chloro-6-fluorobenzaldehyde is observed by gas chromatography. After extraction of the reaction mixture using methyltert-butyl ether, drying of the organic phase over $Na_2SO_4$ and fractional distillation, 31 g (0.238 mol) of 1-chloro-3-fluorobenzene (yield 91.9%) having a content (GC) >99.0% are obtained.

Example 4

Synthesis of 1,2,4,5-tetrafluorobenzene from tetrafluoroterephthalaldehyde

In a glass flask equipped with reflux condenser, stirrer and thermometer, 76 g (0.610 mol) of aqueous KOH solution (45%) are heated to from 90 to 95° C. under argon. With stirring, 42 g (0.204 mol) of tetrafluoroterephthalaldehyde are added in small portions (each approx. 2 g) within 3 hours. On completion of addition, stirring is continued at 95° C. for 15 min. and the mixture is cooled to room temperature. After extraction of a sample of the reaction mixture with diethyl ether, complete conversion of tetrafluoroterephthalaldehyde is detected by gas chromatography. After extraction using diethyl ether, drying of the organic phase over $Na_2SO_4$ and fractional distillation, 25.1 g (0.167 mol) of 1,2,4,5-tetrafluorobenzene (yield 81.9%) are obtained.

What is claimed is:
1. A process for preparing, 1,3-di-halo-substituted benzene derivatives (II) from 2,6-di-halo-substituted benzalde- hydes (I) (where $X_1$, $X_2$ are each independently F, Cl, Br, and $R_1$, $R_2$, $R_3$ are each independently H, halogen, OH, $C_1$–$C_{12}$-alkyl, $CF_3$, CHO, $C_6$–$C_{14}$-aryl, Oalkyl, Oaryl, $NO_2$) by reacting with an alkaline medium, which comprises initially charging the alkaline medium and metering in the 2,6-di-halo-substituted benzaldehyde (I) or initially charging the 2,6-di-halo-substituted benzaldehyde (I) and metering in the alkaline medium

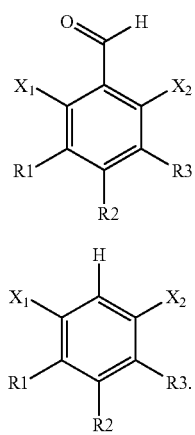

2. The process as claimed in claim 1, wherein the 2,6-di-halo-substituted benzaldehydes (I) used are 2,6-difluorobenzaldehyde, 2-chloro-6-fluorobenzaldehyde, tetrafluoroterephthalaldehyde, 2,4,6-trifluorobenzaldehyde, 4-chloro-2,6-difluorobenzaldehyde, 2,4-dichloro-6-fluorobenzaldehyde, pentafluorobenzaldehyde, 3,5-dichloro-2,4,6-trifluorobenzaldehyde, 2,4,5,6-tetrafluorobenzene-1,3-dicarbaldehyde or 5-chloro-2,4,6-trifluorobenzene-1 3-dicarbaldehyde.

3. The process as claimed in claim 2, wherein the 2,6-di-halo-substituted benzaldehydes (I) used are 2,6-difluorobenzaldehyde, 2-chloro-6-fluorobenzaldehyde or tetrafluoroterephthalaldehyde.

4. The process as claimed in claim 1, wherein the alkaline medium used is an aqueous alkali metal or alkaline earth metal hydroxide or carbonate solution.

5. The process as claimed in claim 1, wherein the reaction is carried out within a temperature range of 50–215° C.

6. The process as claimed in claim 1, wherein the reaction is carried out within a temperature range of 70–160° C.

7. The process as claimed in claim 1, wherein the reaction is carried out under a protective gas.

8. The process as claimed in claim 1, wherein the concentration of the alkaline medium is in the range from 40 to 50% by weight.

9. The process as claimed in claim 1, wherein the yields of the derivatives of the formula (II) are >80%.

10. The process as claimed in claim 3, wherein the alkaline medium used is an aqueous alkali metal or alkaline earth metal hydroxide or carbonate solution.

11. The process as claimed in claim 3, wherein the reaction is carried out within a temperature range of 50–215° C.

12. The process as claimed in claim 11, wherein the reaction is carried out within a temperature range of 70–160° C.

13. The process as claimed in claim 3, wherein the reaction is carried out under a protective gas.

14. The process as claimed in claim 3, wherein the concentration of the alkaline medium is in the range from 40 to 50% by weight.

15. The process as claimed in claim 3, wherein the yields of the defivatives of the formula (II) are >80%.

* * * * *